(12) United States Patent
Rezachek

(10) Patent No.: US 7,958,771 B2
(45) Date of Patent: Jun. 14, 2011

(54) PHOTOACOUSTIC SENSOR

(75) Inventor: Thomas M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 529 days.

(21) Appl. No.: 12/108,430

(22) Filed: Apr. 23, 2008

(65) Prior Publication Data
US 2009/0266144 A1    Oct. 29, 2009

(51) Int. Cl.
*G01N 21/00* (2006.01)
(52) U.S. Cl. ........................................ 73/24.02
(58) Field of Classification Search .............. 73/24.02
See application file for complete search history.

(56) References Cited

U.S. PATENT DOCUMENTS

| | | | |
|---|---|---|---|
| 3,995,960 A | 12/1976 | Fletcher et al. | |
| 4,557,603 A | 12/1985 | Oehler et al. | |
| 5,993,245 A | 11/1999 | Osada | |
| 6,006,585 A * | 12/1999 | Forster | 73/24.01 |
| 7,034,943 B1 * | 4/2006 | Moeckli et al. | 356/423 |
| 7,106,445 B2 * | 9/2006 | Uber | 356/432 |
| 7,398,672 B2 * | 7/2008 | Riddle | 73/24.06 |
| 2004/0145737 A1 | 7/2004 | Hocker | |

FOREIGN PATENT DOCUMENTS

| | | |
|---|---|---|
| EP | 0356536 | 3/1990 |
| EP | 1522778 | 4/2005 |

OTHER PUBLICATIONS

"International Application Serial No. PCT/US2009/002515, International Search Report mailed Jul. 24, 2009", 5 pgs.
"International Application Serial No. PCT/US2009/002515, Written Opinion mailed Jul. 24, 2009", 6 pgs.

* cited by examiner

*Primary Examiner* — John Fitzgerald
(74) *Attorney, Agent, or Firm* — Schwegman, Lundberg & Woessner, P.A.

(57) ABSTRACT

Various embodiments of the application provide a photoacoustic sensor, which includes: a gas cell having an opening; a light source to generate a radiation to radiate sample gas within the gas cell; a detector to detect the sample gas within the gas cell, and to generate electrical signals in response to acoustic signals generated by pressure fluctuations of the radiated sample gas caused by the radiation; and an active valve having a speaker aligned with the opening of the gas cell. The speaker having a voice coil and a diaphragm attached to the voice coil. A control signal is applicable for the speaker to control access of the gas cell. During sampling, the control signal causes the voice coil of the speaker to repeatedly or constantly lift the diaphragm from contact with the opening of the gas cell to allow sample gas enter the gas cell. While during detecting, the spring force of the voice coil causes the diaphragm in tight contact with the opening of gas cell to seal the gas cell.

18 Claims, 3 Drawing Sheets

PHOTOACOUSTIC SENSOR

BACKGROUND

Photoacoustic sensors may be used to detect sample gases based on the tendency of molecules of sample gases, when exposed to certain frequencies of radiant energy, to absorb the energy and reach higher levels of molecular vibration and rotation thereby to reach a higher temperature and pressure. When the radiant energy is amplitude modulated, the resulting fluctuations in energy available for absorption produce corresponding temperature and pressure fluctuations. A sensitive detector can be used to generate an electrical output representing the pressure fluctuations of the sample gases, which can be analyzed to evaluate properties or attributes of the sample gases.

However, it is a challenging task to efficiently and economically control access of the photoacoustic sensors to the sample gases.

BRIEF DESCRIPTION OF THE DRAWINGS

Some embodiments are illustrated by way of examples, and not by way of limitations, in the figures of the accompanying drawings in which.

DETAILED DESCRIPTION

Figure 1:
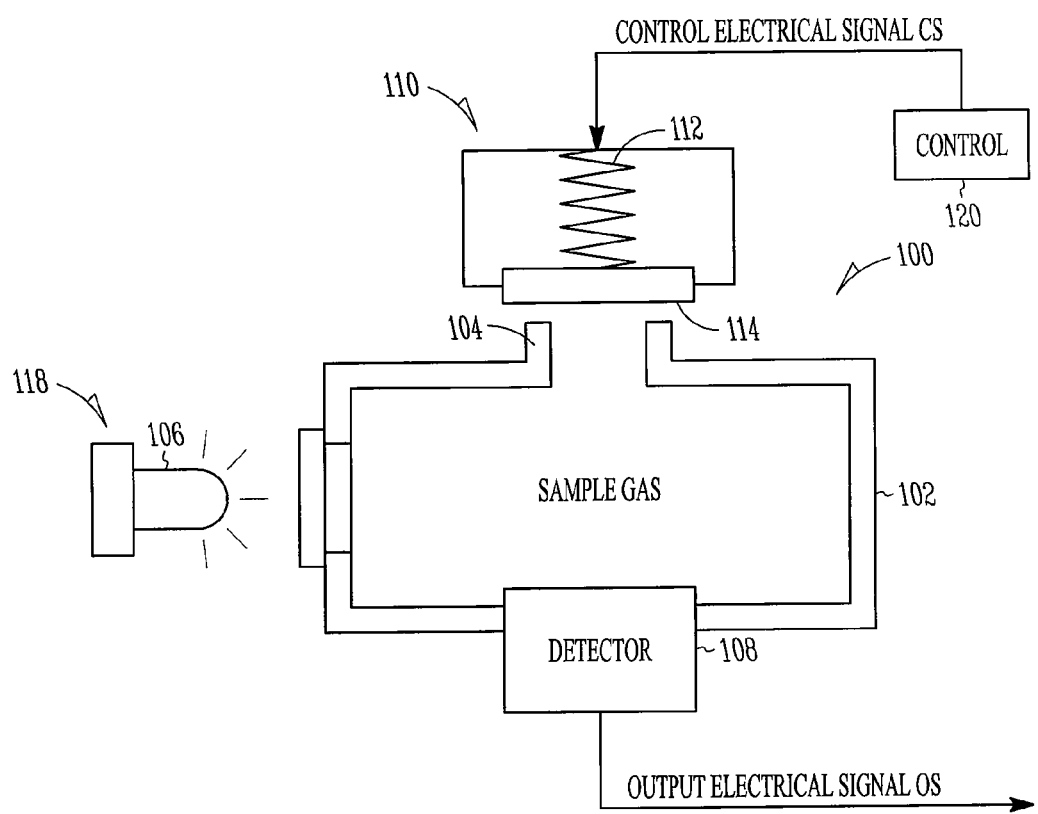
FIG. 1 is a diagram illustrating a photoacoustic sensor according to an example embodiment.

In the following description, for purposes of explanation, numerous specific details are set forth in order to provide a thorough understanding of example embodiments. It will be evident, however, to one skilled in the art that the embodiments of the application may be practiced without these specific details.

Various embodiments described herein utilize photoacoustic gas detection to detect and identify gas samples. One principle of photoacoustic gas detection is based on the measurement of the pressure variation generated in a gas cell or chamber by selective absorption of infrared radiation by the target gas. A measurement includes sampling periods and detecting periods. During detecting, the sample gas in the gas cell may be irradiated with, for example, a modulated narrow-band infrared radiation. The sample gas then heats and cools as incident infrared radiation is modulated. Such temperature fluctuations in turn generate pressure waves, which are detected by a detector, for example a microphone. The microphone generates an electrical output signal, which can be processed and analyzed to identify substances existing in the sample gas and evaluate the properties or attributes, for example the concentration values, of the sample gas collected in the gas cell.

Various embodiments of the application provide a photoacoustic sensor, which includes: a gas cell or chamber having an opening; a light source to generate a radiation to radiate sample gas within the gas cell; a detector to detect the sample gas within the gas cell to generate output electrical signals in response to acoustic signals generated by pressure fluctuations of the radiated sample gas caused by the radiation; and an active valve having a speaker aligned with the opening of the gas cell.

The speaker may have a similar or identical structure to a loudspeaker. For example, the speaker may have a permanent magnet, a voice coil, and a diaphragm (or cone) attached to the voice coil. The speaker can be used to control the access of the gas cell by applying a control signal, which can be either an AC control signal or a DC control signal.

In one example embodiment, an AC control signal is used to control access of the gas cell. During sampling, the AC control signal applies a high voltage to the speaker to cause the voice coil to repeatedly withdraw the diaphragm away from contact with the opening of the gas cell, and thus repeatedly open the gas cell to bring in sample gas from the environment. While during detecting, the AC control signal applies a low voltage to the speaker, and thus the spring force of the voice coil causes the diaphragm to constantly keep in contact with the opening of gas cell to seal the gas cell.

In another example embodiment, a DC control signal is used to control access to the gas cell. During sampling, the DC control signal applies a bias to speaker to withdraw the voice coil into the speaker, causes the attached diaphragm to be away from contact with the opening of the gas cell, and thus opens the gas cell to bring in sample gas from the environment. While during detecting, the DC control signal applies no bias to the speaker, and thus the spring force of the voice coil pushes the diaphragm to be in contact with the opening of gas cell to seal the gas cell.

FIG. 1 is a block diagram of a photoacoustic sensor 100 according to an example embodiment. The photoacoustic sensor 100 may comprise: a gas cell 102 with an opening 104; a light source 106 to generate a radiation to radiate sample gas within the gas cell 102; a detector 108 to detect the sample gas within the gas cell 102; and an active valve having a speaker 110 aligned with the opening 104 of the gas cell 102. The detector 108 may be for example a microphone, which may generate electrical output signals OS in response to acoustic signals generated by pressure fluctuations of the radiated sample gas caused by the radiation from the light source 106. In one embodiment, the microphone 108 is provided access to pressure variations in the sample gas, yet provides a seal to prevent gas from entering or escaping from gas cell 102 other than by the opening 104.

In some embodiments, the photoacoustic sensor 100 may further comprise a light filter 116, which is positioned between the light source 106 and the gas cell 102 to filter the radiation into the gas cell. In some embodiments, a modulator 118 may be used to modulate the radiation generated by the light source 106 during detecting the sample gas. In one embodiment, the light filter 116 also provides a seal to prevent gas from entering or escaping from gas cell 102 other than by the opening 104.

In some embodiments, the speaker 110 of the photoacoustic sensor 100 may include a permanent magnet (not shown in FIG. 1), a voice coil 112 around the permanent magnet, and a diaphragm 114 attached to the voice coil 112. The speaker 110, for example, may be aligned relative to the gas cell 102 such that during detecting the central portion of the diaphragm 114 may come into contact with the edge of the opening 104 of the gas cell 102, and thus may seal the gas cell 102.

In some embodiments, in order to enhance or improve the sealing effects, the surface of the diaphragm 114 of the speaker 110, which faces the opening 104 of the gas cell 102, may be coated with a layer of material, for example, a light oil material or a soft rubber, to ensure a close contact between the diaphragm 114 and the opening 104 of the gas cell 102 during detecting. Because the gas cell 102 remains tightly sealed during detecting, the impact of the acoustic noise upon the detection is reduced, and thus the signal-to-noise ratio of the detection is raised.

Figure 2:
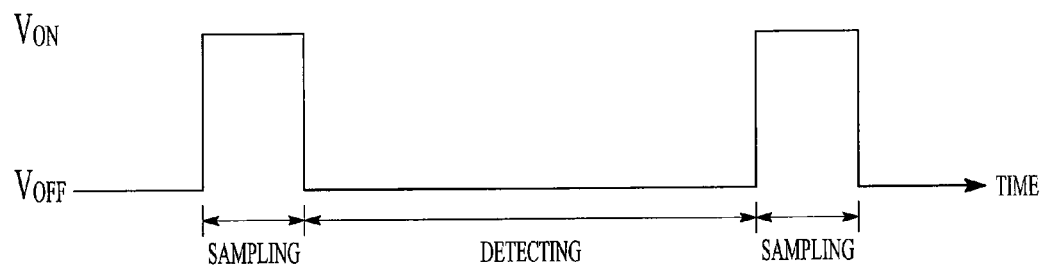
FIG. 2 is a diagram illustrating a control signal to control the access of a gas cell of the photoacoustic sensor as shown in FIG. 1 according to an example embodiment.

FIG. 2 is a diagram illustrating a control signal CS, which has a high voltage level $V_{on}$ and a low voltage level $V_{off}$, to control the access of the gas cell 102 according to an example embodiment. The control signal CS for example can be applied to the speaker 110 to control access of the gas cell 102, such that during sampling the gas cell 102 is repeatedly or constantly open and thus sample gas may enter into the gas cell 102, while during detecting the gas cell 102 remains constantly sealed. The control signal CS can be, for example, either an AC control signal or a DC control signal.

In one example embodiment, a DC control signal CS is used to control access of the gas cell 100. During sampling, the DC control signal CS applies a bias $V_{on}$ to the voice coil 112 of speaker 110 to withdraw the voice coil 112 into the speaker 110 to lift the diaphragm 114 from contact with the opening 104 of the gas cell 102, and thus causes the gas cell 110 open to allow sample gas enter the gas cell 102 from the environment. While during detecting, the DC control signal CS applies no bias $V_{off}$ to the speaker 110, and the spring force of the voice coil 112 pushes the diaphragm 114 in contact with the opening 104 of gas cell 102, and thus seals the gas cell 102.

In another example embodiment, an AC control signal CS is used to control access of the gas cell 100. During sampling, the AC control signal CS is set at $V_{on}$ to cause a vibration of the voice coil 112, which causes the diaphragm 114 (attached to the voice coil 112) to move back and forth from the opening 104 of the gas cell 102, and thus repeatedly to open and close the opening 104 of the gas cell 102 to bring new sample gas into the gas cell 102 at a selected operation frequency. While during detecting, the AC control signal CS is set at $V_{off}$, and the spring force of the voice coil 112 pushes the diaphragm 114 in contact with the opening 104 of gas cell 102, and thus seals the gas cell 102.

For example, the AC control signal CS may have a drive frequency, for example less than 10 Hz. The operation frequency of the diaphragm 114 may be selected to be at a level of sub-audible frequency, for example about 0.1 Hz.

In one embodiment, the control signal CS comes from a separate control device or controller 120, such as an integrated circuit. In further embodiments, a computer based algorithm that may receive the output signal from the detector 108 or modulator 118 and generate the control signal as function of such inputs. In another embodiment, the control signal CS comes from the modulator 118. In still another embodiment, the control signal CS is a portion of the electrical output signal OS, which is generated by the microphone 108.

Figure 3:
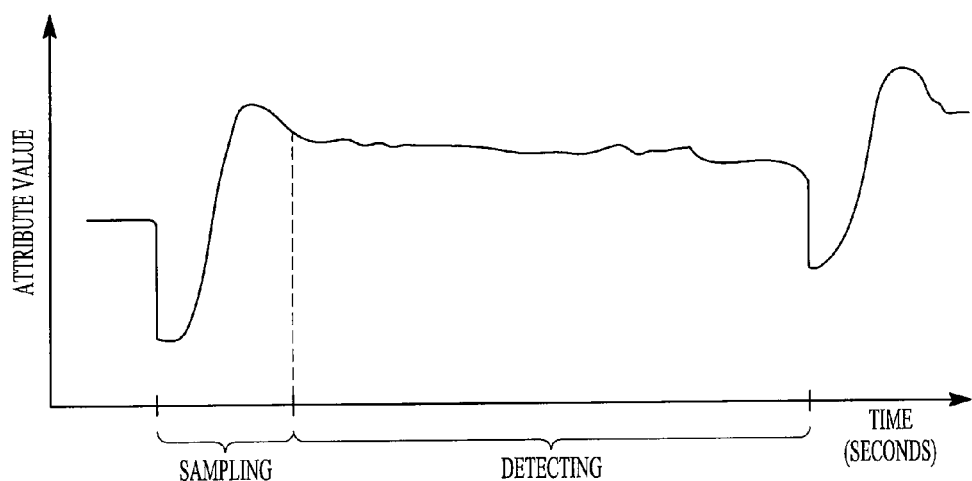
FIG. 3 is a diagram illustrating an electrical output signal of the photoacoustic sensor as shown in FIG. 1 during a measurement period according to an example embodiment.

FIG. 3 is a diagram illustrating an electrical output signal OS of the photoacoustic sensor 100 as shown in FIG. 1 during a measurement period according to an example embodiment. Within the measurement period, there are two states, either a sampling state or a detecting state.

During detecting, the microphone 108 may detect the sample gas within the gas cell 102, and generate an output electrical signals OS in response to acoustic signals generated by pressure fluctuations of the radiated sample gas caused by the radiation. The electrical output signal OS can be used to analyze attributes (e.g., concentration) of the sample gas inside the gas cell 102.

For example, during detecting, an infrared light source 106 may be modulated to radiate the sample gas in the gas cell 102 to cause the sample gas within the gas cell 102 to heat and cool as incident infrared radiation is modulated. These temperature fluctuations in turn generate pressure waves, which may be detected by the microphone 108, and thus generate an electrical output signal OS. The electrical output signal OS from the microphone 108 can be processed and analyzed to evaluate the properties or attributes of the sample gas sealed in the gas cell 102. For example, by analyzing an obtained spectrum of the sample gas sealed in the gas cell 102, users may identify substances existing in the sample gas, and determine the concentration of the substances in the sample gas within the gas cell 102. Various known techniques may be used to detect the properties or attributes of the sample gas by using the photoacoustic sensor of the present application.

The sampling states and detecting states within a measurement period, for example, can be controlled by the control signal as shown in FIG. 2. A sampling state occurs when the speaker 110 opens the gas cell 102. At this time sample gas enters the gas cell 102. A detection state occurs when the speaker seals the gas cell 102. A brief delay may be applied to exclude the pressure transient that may occur as the speaker closes the gas cell 102. Following this delay, the electrical output signals OS from the microphone 108 will be sampled and processed to derive the current gas concentration. The various state times will be derived from the light source drive signal. For example, with an 8 Hz light source drive frequency, the sampling state will be about 1 second or 8 light source cycles, and the detection state will be about 9 seconds or 72 lamp cycles. These times can be adjusted to produce the desired sensitivity and response. A new concentration value of the sample gas can be detected at the end of each detection state.

In some embodiments, controller 120 may be used to control the operation of the modulator 118, light source 106, active valve and detector 108 to operate in the manner described for various embodiments.

Figure 4:
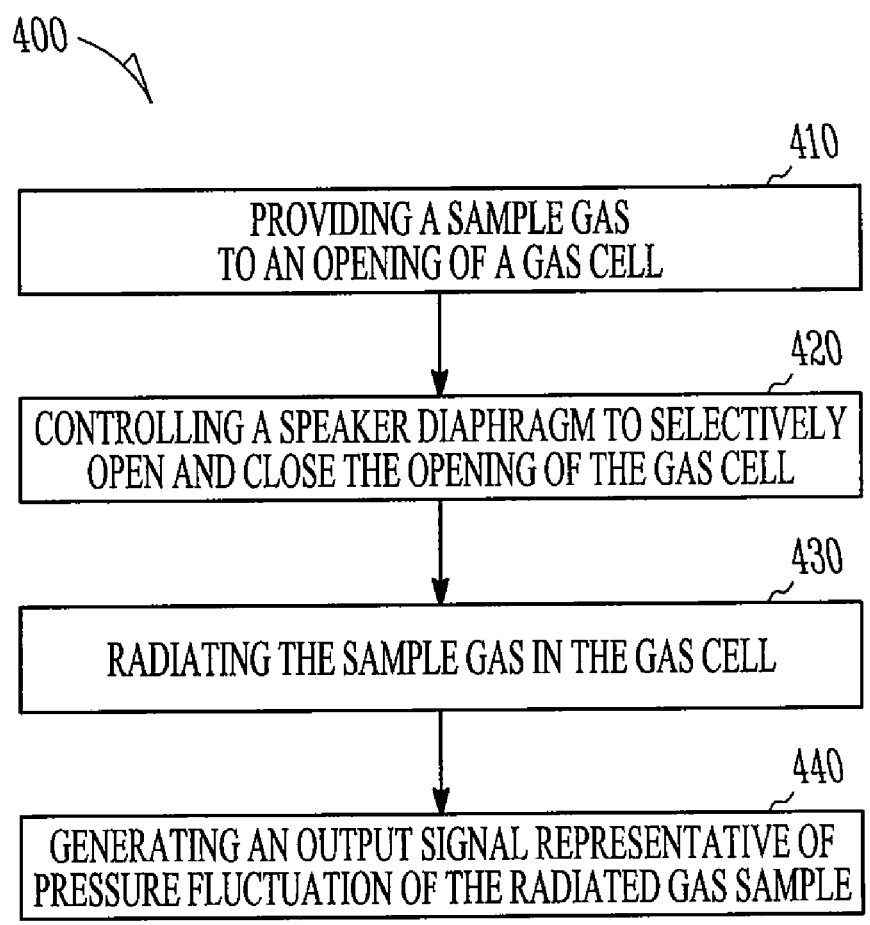
FIG. 4 is a flow diagram illustrating a method of detecting a sample gas by using the photoacoustic sensor as shown in FIG. 1 according to an example embodiment.

FIG. 4 is a flow diagram illustrating a method 400 of detecting a sample gas by using the photoacoustic sensor as shown in FIG. 1 according to an embodiment.

At block 410, a sample gas is provided to the opening 104 of the gas cell 102.

At block 420, the speaker diaphragm 114 of the speaker 110 is controlled to selectively open and close the opening 104 of the gas cell 102.

At block 430, the sample gas in the gas cell 102 is radiated.

At block 440, an output signal representative of pressure fluctuation of the radiated gas sample is generated.

In some embodiments, the speaker 110 is controlled by an AC control signal applied to the speaker voice coil 112 attached to the speaker diaphragm 114. The AC control signal may open and close the opening 104 of the gas cell 102, for example, at a frequency of less than 10 Hz.

In some embodiments, the speaker diaphragm 114 is mechanically biased to close the gas cell opening when no control signal is applied to the voice coil.

While there has been described herein the principles of the application, it is to be understood by those skilled in the art that this description is made only by way of example and not as a limitation to the scope of the application. Accordingly, it is intended by the appended claims, to cover all modifications of the application which fall within the true spirit and scope of the application.

The invention claimed is:

1. A photoacoustic sensor, comprising:
  a gas cell having an opening;

a light source to generate radiation to radiate sample gas within the gas cell;

a detector to detect the sample gas within the gas cell, and to generate output electrical signals in response to acoustic signals generated by pressure fluctuations of the radiated sample gas caused by the radiation;

an active valve having a speaker aligned with the opening of the gas cell, the speaker having a voice coil and a diaphragm attached to the voice coil to control access to the gas cell; and a modulator to modulate the radiation generated by the light source, wherein the modulator generates a control signal to control the active valve.

2. The photoacoustic sensor of claim 1, wherein during sampling, a control signal biases the speaker to lift the diaphragm from contact with the opening of the gas cell to open the gas cell, and during detecting, the control electrical signal applies no bias to the speaker to maintain the diaphragm in contact with the opening of the gas cell to seal the gas cell.

3. The photoacoustic sensor of claim 1, further comprising a light filter positioned between the light source and the gas cell to filter the radiation radiated into the gas cell.

4. The photoacoustic sensor of claim 1, wherein a surface of the diaphragm facing the opening of the gas cell is coated with a layer of light oil or rubber.

5. The photoacoustic sensor of claim 1, wherein the detector is a microphone.

6. The photoacoustic sensor of claim 1, further comprising a control device to generate a control signal to control the active valve.

7. A photoacoustic sensor, comprising:

a gas cell having an opening;

a light source to generate radiation to radiate sample gas within the gas cell;

a detector to detect the sample gas within the gas cell, and to generate output electrical signals in response to acoustic signals generated by pressure fluctuations of the radiated sample gas caused by the radiation; and an active valve having a speaker aligned with the opening of the gas cell, the speaker having a voice coil and a diaphragm attached to the voice coil to control access to the gas cell, wherein a control signal to control the active valve comprises a portion of the output electrical signals generated by the detector.

8. A photoacoustic sensor, comprising:

a gas cell having an opening;

a light source to generate a radiation to radiate sample gas within the gas cell;

a detector to detect the sample gas within the gas cell, and to generate output electrical signals in response to acoustic signals generated by pressure fluctuations of the radiated sample gas caused by the radiation;

an active valve having a speaker aligned with the opening of the gas cell, the speaker having a voice coil and a diaphragm attached to the voice coil;

means for generating an AC control signal to control access to the gas cell, wherein during sampling, the AC control signal is set on to generate a vibration of the diaphragm to repeatedly open and close the opening of the gas cell at an operation frequency selected to bring new sample gas into the gas cell, and during detecting, the AC control signal is set off to close the opening of the gas cell; and a modulator to modulate the radiation generated by the light source, wherein the modulator generates a control signal to control the active valve.

9. The photoacoustic sensor of claim 8, further comprising a light filter positioned between the light source and the gas cell to filter the radiation into the gas cell.

10. The photoacoustic sensor of claim 8, wherein the AC control signal is applicable to the voice coil of the speaker to control access of the gas cell.

11. The photoacoustic sensor of claim 8, wherein the AC control signal has a drive frequency.

12. The photoacoustic sensor of claim 8, wherein the operation frequency of the diaphragm is set at a level of sub-audible frequency.

13. The photoacoustic sensor of claim 8, wherein a surface of the diaphragm facing the opening of the gas cell is coated with a layer of light oil or rubber.

14. The photoacoustic sensor of claim 8, wherein the detector is a microphone.

15. A method comprising:

providing a sample gas to an opening of a gas cell;

controlling a speaker diaphragm by an AC control signal to selectively open and close the opening of the gas cell;

radiating the sample gas in the gas cell; and generating, by a detector, an output electrical signal representative of pressure fluctuation of the radiated gas sample, wherein the AC control signal comprises a portion of the output electrical signals generated by the detector.

16. The method of claim 15, wherein the speaker diaphragm is controlled by an AC control signal applied to a voice coil attached to the speaker diaphragm.

17. The method of claim 16, wherein the AC control signal opens and closes the opening of the gas cell at a frequency.

18. The method of claim 17, wherein the speaker diaphragm is mechanically biased to close the gas cell opening when no control signal is applied to the voice coil.

* * * * *